United States Patent [19]

Caldwell et al.

[11] Patent Number: 5,214,060

[45] Date of Patent: May 25, 1993

[54] METHOD FOR TREATMENT OF NEURODEGENERATIVE DISEASES

[75] Inventors: William S. Caldwell, Winston-Salem; Patrick M. Lippiello, Clemmons, both of N.C.

[73] Assignee: R. J. Reynolds Tobacco Company, Winston-Salem, N.C.

[21] Appl. No.: 866,594

[22] Filed: Apr. 10, 1992

[51] Int. Cl.$^5$ .............................................. A61K 31/44
[52] U.S. Cl. .................................................. 514/343
[58] Field of Search ........................................ 514/343

[56] References Cited

U.S. PATENT DOCUMENTS

| | | |
|---|---|---|
| 3,870,794 | 3/1975 | Hutchinson et al. . |
| 4,342,762 | 8/1982 | Budai et al. . |
| 4,442,292 | 4/1984 | Edwards, III . |
| 4,578,394 | 3/1986 | Allen et al. . |
| 4,765,985 | 8/1988 | Leeson . |
| 4,863,930 | 9/1989 | Adhikary . |
| 4,965,074 | 10/1990 | Leeson . |
| 5,015,741 | 5/1991 | Osdene et al. . |

OTHER PUBLICATIONS

Benwell M. et al., "Evidence that Tobacco Smoking Increases the Density of (−)-[$^3$H] Nicotine Binding Sites in Human Brain", *Journal of Neurochemistry*, vol. 50, pp. 1243–1247 (1988).

Hodges H. et al., "Nicotine as a Tool to Charcterize the Role of the Forebrain Cholinergic Projection System in Cognition", *Biology of Nicotine*, pp. 157–181 (1992).

Janson A. et al., "Protective effects of chronic nicotine treatment on lesioned nigrostriatal dopamine neurons in the male rat", *Progress in Brain Research*, vol. 79, pp. 257–265 (1989).

Newhouse P. et al., "Intravenous nicotine in Alzheimer's disease: a pilot study", *Psychopharmocology*, vol. 95, pp. 171–175 (1988).

Nordberg A. et al., "The Role of Nicotine Receptors in the Pathophysiology of Alzheimer's Disease", *Progress In Brain Research*, vol. 79, pp. 353–362 (1989).

Rinne J. et al., "A postmortem study of brain nicotinic receptors in Parkinson's and Alzheimer's disease", *Brain Research*, vol. 547, pp. 167–170 (1991).

Rowell P. et al., "Nicotinic Stimulatoin of [$^3$H] Acetylcholine Release from Mouse Cerebral Cortical Synaptosomes", *Journal of Neurochemistry*, vol. 43, pp. 1593–1598 (1984).

van Duijan C. et al., "Relation between nicotine intake and Alzheimer's disease", *BMJ*, vol. 302, pp. 1491–1494 (1991).

*Primary Examiner*—S. J. Friedman

[57] ABSTRACT

Patients suffering from neurodegenerative diseases are treated by administering an effective amount of a pyridylalkylpiperidine compound or a pyridylalkylpyrrolidine compound.

18 Claims, No Drawings

METHOD FOR TREATMENT OF NEURODEGENERATIVE DISEASES

BACKGROUND OF THE INVENTION

The present invention relates to a method for treating patients having neurodegenerative diseases, and in particular, to a method for treating patients suffering from those diseases which cause a cholinergic deficit.

Senile dementia of the Alzheimer's type (SDAT) is a debilitating neurodegenerative disease, mainly afflicting the elderly; characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, Jones, et al., *Intern. J. Neurosci.*, Vol. 50, p. 147 (1990); Perry, *Br. Med. Bull.*, Vol. 42, p. 63 (1986) and Sitaram, et al., *Science*, Vol. 201, p. 274 (1978). It has been observed that nicotinic acetylcholine receptors, which bind nicotine and other nicotinic agonists with high affinity, are depleted during the progression of SDAT. See, Giacobini, *J. Neurosci. Res.*, Vol. 27, p. 548 (1990); and Baron, *Neurology*, Vol. 36, p. 1490 (1986). As such, it would seem desirable to provide therapeutic compounds which either directly activate nicotinic receptors in place of acetylcholine or act to minimize the loss of those nicotinic receptors.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., *Brain Res.*, Vol. 54, pp. 167-170 (1991) and Clark, et al., *Br. J. Pharm.*, Vol. 85, pp. 827-835 (1985).

Certain attempts have been made to treat SDAT. For example, nicotine has been suggested to possess an ability to activate nicotinic cholinergic receptors upon acute administration, and to elicit an increase in the number of such receptors upon chronic administration to animals. See, Rowell, *Adv. Behav. Biol.*, Vol. 31, p. 191 (1987); and Marks, *J. Pharmacol. Exp. Ther.*, Vol. 226, p. 817 (1983). Other studies indicate that nicotine can act directly to elicit the release of acetylcholine in brain tissue, to improve cognitive functions, and to enhance attention. See, Rowell, et al., *J. Neurochem.*, Vol. 43, p. 1593 (1984); Hodges, et al., *Bio. of Nic.*, Edit. by Lippiello, et al., p. 157 (1991); Sahakian, et al., *Br. J. Psych.*, Vol. 154, p. 797 (1989); and U.S. Pat. No. 4,965,074 to Leeson.

It would be desirable to provide a method for treating neurodegenerative diseases, such as SDAT and PD, by administering a nicotinic compound to the patient suffering from such disease.

SUMMARY OF THE INVENTION

The present invention relates to a method for the treatment of a neurodegenerative disease. The method involves treating a patient suffering from such disease (e.g., SDAT or PD) with an effective amount of a pyridylalkylpiperidine compound or a pyridylalkylpyrrolidine compound.

The method of the present invention provides benefits to the patient in that the compounds have the potential to (i) act as a pharmacological agonist to activate nicotinic receptors, and (ii) elicit neurotransmitter secretion. In addition, the compounds are expected to have the potential to (i) increase the number of nicotinic cholinergic receptors of the brain of the patient, and (ii) exhibit neuroprotective effects.

DETAILED DESCRIPTION OF THE PREFERRED EMBODIMENTS

The present invention relates to a method for the treatment of neurodegenerative diseases, such as SDAT and PD. In particular, the method involves treating a patient with an effective amount of a compound having the general formula:

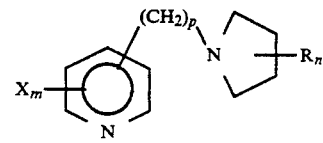

where R represents a substituent other than hydrogen (e.g., alkyl, such as lower straight chain or branched alkyl, including $C_1$-$C_7$); X is a substituent other than hydrogen (e.g., halo, such as F, Cl, Br or I; or alkyl, such as lower straight chain or branched alkyl, including $C_1$-$C_7$); and p is an integer which can range from 1-5. One or more of the carbon atoms of the pyridine ring and/or one or more of the carbon atoms of the pyrrolidine ring can include substituent groups other than hydrogen (e.g., halo or alkyl substituents in the case of the pyridine ring; and alkyl substituents in the case of the pyrrolidine ring. As such, m is an integer which can range from 0-4, and n is an integer which can range from 0-8, preferably 0-4. The alkyl pyrrolidine substituent can be positioned at the 2 or 3 position of the pyridine ring. See, Haglid et al., *Acta Pharm. Svec.*, Vol. 4, p.117 (1967).

In another aspect, the method involves treating a patient with an effective amount of a compound having the formula:

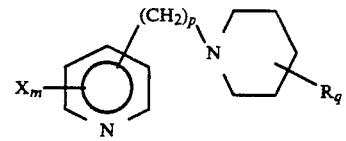

where X, R, m and p are previously defined; and q is an integer which can range from 0-10, preferably 0-5. The alkyl-piperidine substituent can be positioned at the 2 or 3 position of the pyridine ring. See, Robertson et al., *J. Med. Chem.*, Vol. 6, p.805 (1963).

The compounds can be employed as racemic mixtures or as enantiomers. The compounds can be employed in salt form (e.g., as chloride, sulfate, tartrate, fumarate, citrate, malate, lactate or aspartate salts).

The manner in which the compounds are administered can vary. The compounds can be administered by inhalation; in the form of an aerosol either nasally or using delivery articles of the type set forth in U.S. Pat.

Nos. 4,922,901 to Brooks, et al. and 5,099,861 to Clearman et al.; orally (e.g., in liquid form within a solvent such as an aqueous liquid, or within a solid carrier); intravenously (e.g., within a saline solution); or transdermally (e.g., using a transdermal patch). Exemplary methods for administering such compounds will be apparent to the skilled artisan. Certain methods suitable for administering compounds useful according to the present invention are set forth in U.S. Pat. No. 4,965,074 to Leeson. The administration can be intermittent, or at a gradual, continuous, constant or controlled rate to a warm-blooded animal, such as a human being or other mammal.

The dose of the compound is that amount effective to treat the neurodegenerative disease from which the patient suffers. By "effective amount" or "effective dose" is meant that amount sufficient to pass across the blood-brain barrier of the patient, to bind to relevant receptor sites in the brain of the patient, and to elicit neuropharmacological effects (e.g., elicit neurotransmitter secretion, thus resulting in effective treatment of the disease). Treatment of a neurodegenerative disease involves a decrease of symptoms of the particular disease.

For human patients, the effective dose of typical compounds generally does not exceed about 150 $\mu$g, often does not exceed about 100 $\mu$g, and frequently does not exceed about 50 $\mu$g, per kg patient weight. For human patients, the effective dose of typical compounds generally is at least about 5 $\mu$g, often is at least about 10 $\mu$g, and frequently is at least about 25 $\mu$g, per kg of patient weight. For human patients, the effective dose of typical compounds generally requires administering the compound in an amount of at least about 2.0, often at least about 1.0, and frequently at least about 0.1 mg/hr/patient. For human patients, the effective dose of typical compounds requires administering the compound in an amount which generally does not exceed about 10, often does not exceed about 5, and frequently does not exceed about 2.5 mg/hr/patient.

The compounds useful according to the method of the present invention have the ability to pass across the blood-brain barrier of the patient. As such, such compounds have the ability to enter the central nervous system of the patient. The log P values of typical compounds useful in carrying out the present invention generally are greater than 0, often are greater than about 0.1, and frequently are greater than about 0.5. The log P values of such typical compounds generally are less than about 3.0, often are less than about 2.5, and frequently are less than about 2.0. Log P values provide a measure of the ability of a compound to pass across a diffusion barrier, such as a biological membrane. See, Hansch, et al., *J. Med. Chem.*, Vol. 11, p. 1 (1968).

The compounds useful according to the method of the present invention have the ability to bind to, and hence cause activation of, nicotinic cholinergic receptors of the brain of the patient. As such, such compounds have the ability to act as nicotinic agonists. The receptor binding constants of typical compounds useful in carrying out the present invention generally exceed about 1 nM, often exceed about 200 nM, and frequently exceed about 500 nM. The receptor binding constants of such typical compounds generally are less than about 10 $\mu$M, often are less than about 7 $\mu$M, and frequently are less than about 2 $\mu$M. Receptor binding constants provide a measure of the ability of the compound to bind to half of the relevant receptor sites of certain brain cells of the patient. See, Cheng, et al., *Biochem. Pharmacol.*, Vol. 22, pp. 3099–3108 (1973).

The compounds useful according to the method of the present invention have the ability to demonstrate a nicotinic function by effectively eliciting neurotransmitter secretion from nerve ending preparations (i.e., synaptosomes). As such, such compounds have the ability to cause relevant neurons to release or secrete acetylcholine, dopamine, and other neurotransmitters. Generally, typical compounds useful in carrying out the present invention provide for the secretion of dopamine in amounts of at least about 3 percent, often at least about 25 percent, and frequently at least about 50 percent, of that elicited by an equal molar amount of (S)-(−)-nicotine.

The following example is provided in order to further illustrate various embodiments of the invention but should not be construed as limiting the scope thereof. Unless otherwise noted, all parts and percentages are by weight.

EXAMPLE 1

Mice (DBA strain) were maintained on a 12 hour light/dark cycle and were allowed free access to water and food supplied by Wayne Lab Blox, Madison, Wis. Animals used in the present studies were 60 to 90 days of age and weighed 20 to 25 g. Brain membrane preparations were obtained from pooled brain tissue of both males and females.

Mice were killed by cervical dislocation. Brains were removed and placed on an ice-cold platform. The cerebellum was removed and the remaining tissue was placed in 10 volumes (weight:volume) of ice-cold buffer (Krebs-Ringers HEPES:NaCl, 118 mM; KCl, 4.8 mM; $CaCl_2$, 2.5 mM; $MgSO_4$, 1.2 mM; HEPES, 20 mM; pH to 7.5 with NaOH) and homogenized with a glass-Teflon tissue grinder. The resulting homogenate was centrifuged at 18000 x g for 20 min. and the resulting pellet was resuspended in 20 volumes of water. After 60 min. incubation at 4° C., a new pellet was collected by centrifugation at 18000 x g for 20 min. After resuspension in 10 volumes of buffer, a new final pellet was again collected by centrifugation at 18000 x g for 20 min. Prior to each centrifugation step, the suspension was incubated at 37° C. for 5 min. to promote hydrolysis of endogenous acetylcholine. The final pellet was overlayered with buffer and stored at −70° C. On the day of the assay, that pellet was thawed, resuspended in buffer and centrifuged at 18000 x g for 20 min. The resulting pellet obtained was resuspended in buffer to a final concentration of approximately 5 mg protein/ml. Protein was determined by the method of Lowry, et al., *J. Biol. Chem.*, Vol. 193, pp. 265–275 (1951), using bovine serum albumin as the standard.

The binding of L-[$^3$H]nicotine was measured using a modification of the method of Romano, et al., *Science*, Vol. 210, pp. 647–650 (1980) as described previously by Marks, et al., *Mol. Pharmacol.*, Vol. 30, pp. 427–436 (1986). The binding of L-[$^3$H] nicotine was measured using a 2 hr. incubation at 4° C. Incubations contained about 500 $\mu$g of protein and were conducted in 12 mm $\times$ 75 mm polypropylene test tubes in a final incubation volume of 250 $\mu$l. The incubation buffer was Krebs-Ringers HEPES containing 200 mM TRIS buffer, pH 7.5. The binding reaction was terminated by filtration of the protein containing bound ligand onto glass fiber filters (Micro Filtration Systems) that had been soaked in buffer containing 0.5 percent polyethyleneimine.

Filtration vacuum was −50 to −100 torr. Each filter was washed five times with 3 ml of ice-cold buffer. The filtration apparatus was cooled to 2° C. before use and was kept cold through the filtration process. Nonspecific binding was determined by inclusion of 10 μM non-radioactive nicotine in the incubations. The inhibition of L-[$^3$H]nicotine binding by test compounds was determined by including one of eight different concentrations of the test compound in the incubation. Inhibition profiles were measured using 10 nM L-[$^3$H]nicotine and IC$_{50}$ values were estimated as the concentration of compound that inhibited 50 percent of specific L-[$^3$H]nicotine binding. Inhibition constants (Ki values) were calculated from the IC$_{50}$ values using the method of Cheng, et al., Biochem. Pharmacol., Vol. 22, pp. 3099-3108 (1973). The Ki values for all compounds for which an inhibition constant less than 100 μM was determined from the inhibition curves described above were also calculated independently using Dixon plots for inhibition measured using 2 nM, 8 nM and 20 nM concentrations of L-[$^3$H]nicotine. The L-[$^3$H]nicotine used in all experiments was purified chromatographically by the method of Romm, et al., Life Sci., Vol. 46, pp. 935-943 (1990).

Log P values (log octanol/water partition coefficient), which have been used to assess the relative abilities of compounds to pass across the blood-brain barrier, were calculated according to the methods described by Hansch, et al., J. Med. Chem., Vol. 11, p. 1 (1968).

Dopamine release was measured by preparing synaptosomes from the striatal area of rat brain obtained from Sprague-Dawley rats generally according to the procedures set forth by Nagy, et al., J. Neurochem., Vol. 43, pp. 1114-1123 (1984). Striata from 4 rats were homogenized in 2 ml of 0.32M sucrose buffered with 5 mM HEPES (pH 7.5), using a glass-teflon tissue grinder. The homogenate was diluted to 5 ml with additional homogenization solution and centrifuged at 1000 x g for 10 min. This procedure was repeated on the new pellet and the resulting supernatant was centrifuged at 12,000 x g for 20 min. A 3 layer discontinuous Percoll gradient consisting of 16 percent, 10 percent and 7.5 percent Percoll in HEPES-buffered sucrose was made with the final pellet dispersed in the top layer. After centrifugation at 15,000 x g for 20 min., the synaptosomes were recovered above the 16 percent layer with a pasteur pipette, diluted with 8 ml of perfusion buffer (128 mM NaCl, 2.4 mM KCl, 3.2 mM CaCl$_2$, 1.2 mM KH$_2$PO$_4$, 1.2 mM MgSO$_4$, 25 mM HEPES pH 7.4, 10 mM dextrose, 1 mM ascorbate, 0.01 mM pargyline), and centrifuged at 15,000 x g for 20 min. The new pellet was collected and re-suspended in perfusion buffer. The synaptosome suspension was incubated for 10 min. at 37° C. Then [$^3$H]-dopamine (Amersham, 40-60 Ci/mmol) was added to the suspension to give a final concentration of 0.1 μM in suspension, and the suspension was incubated for another 5 min. Using this method, 30 to 90 percent of the dopamine was taken up into the synaptosomes, as determined by scintillation counting following filtration through glass fiber filters soaked with 0.5 percent polyethyleneimine. A continuous perfusion system was used to monitor release following exposure to each ligand (i.e., 2-pyridyl-ethylpiperidine, and 3-pyridylmethylpyrrolidine). Synaptosomes were loaded onto glass fiber filters (Gelman type A/E). Perfusion buffer was dripped onto the filters (0.2-0.3 ml/min.) and pulled through the filters with a peristaltic pump. Synaptosomes were washed with perfusion buffer for a minimum of 20 min. before addition of the ligand. After the addition of a 0.2 ml of a 20 μM solution of ligand, the perfusate was collected into scintillation vials at 1 min. intervals and the dopamine released was quantified by scintillation counting. Peaks of radioactivity released above background were summed and the average basal release during that time was subtracted from the total. Release was expressed as a percentage of release obtained with an equal concentration of (S)-(−)-nicotine.

Data regarding octanol-water partition coefficients, binding constants and neurotransmitter secretion capability for the ligands evaluated are set forth in Table I.

TABLE I

| Compound | Ki (nM)[1] | Log P | Dopamine[2] Release |
|---|---|---|---|
| 2-pyridylethylpiperidine | 6,500 | 2.0 | 5 |
| 3-pyridylmethylpyrrolidine | 49 | 1.3 | 80 |

[1]Concentration of compound which inhibits 50 percent of L-[$^3$H]nicotine binding.
[2]Percent release relative to (S)-(−)-nicotine.

The data in Table I indicate that the compounds have the capability of passing the blood-brain barrier, binding to high affinity nicotinic receptors, and eliciting neurotransmitter secretion. Thus, the data indicate that such compounds have the capability of being useful in treating neurodegenerative diseases.

What is claimed is:

1. A method for treating a patient suffering from senile dementia of the Alzheimer's type, the method comprising administering to the patient an effective amount of a compound having the formula:

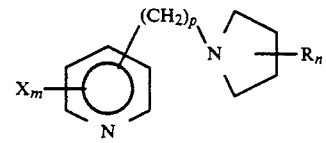

where R and X each represent a substituent other than hydrogen, m is an integer from 0-4, n is an integer from 0-8, p is an integer from 1-5, and the alkylpyrrolidine substituent is positioned at the 2 or 3 position of the pyridine ring.

2. A method for treating a patient suffering from senile dementia of the Alzheimer's type, the method comprising administering to the patient an effective amount of a compound having the formula:

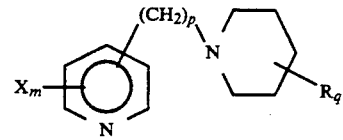

where R and X each represent a substituent other than hydrogen, m is an integer from 0-4, q is an integer from 0-10, p is an integer from 1-5, and the alkylpiperidine substituent is positioned at the 2 or 3 position of the pyridine ring.

3. The method of claim 1 or 2 whereby the effective amount of the compound is at least about 5 μg/kg patient weight, but does not exceed about 150 μg/kg patient weight.

4. The method of claim 1 or 2 whereby the effective amount of compound is administered to the patient in an amount of at least about 0.10 mg/hr/patient, but in an amount which does not exceed about 10 mg/hr/patient.

5. A method for treating a patient suffering from Parkinson's disease, the method comprising administering to the patient an effective amount of a compound having the formula:

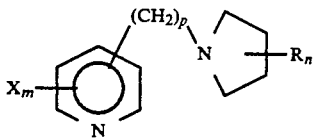

where R and X each represent a substituent other than hydrogen, m is an integer from 0–4, n is an integer from 0–8, p is an integer from 1–5, and the alkylpyrrolidine substituent is positioned at the 2 or 3 position of the pyridine ring.

6. A method for treating a patient suffering from Parkinson's disease, the method comprising administering to the patient an effective amount of a compound having the formula:

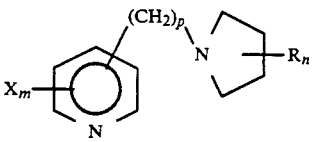

where R and X each represent a substituent other than hydrogen, m is an integer from 0–4, q is an integer from 0–10, p is an integer from 1–5, and the alkylpiperidine substituent is positioned at the 2 or 3 position of the pyridine ring.

7. The method of claim 5 or 6 whereby the effective amount of the compound is at least about 5 μg/kg patient weight, but does not exceed about 150 μg/kg patient weight.

8. The method of claim 5 or 6 whereby the effective amount of compound is administered to the patient in an amount of at least about 0.10 mg/hr/patient, but in an amount which does not exceed about 10 mg/hr/patient.

9. A method for treating a patient suffering from a neurodegenerative disease, the method comprising administering to the patient an effective amount of a compound having the formula:

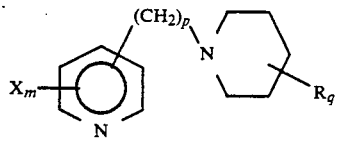

where R and X each represent a substituent other than hydrogen, m is an integer from 0–4, n is an integer from 0–8, p is an integer from 1–5, and the alkylpyrrolidine substituent is positioned at the 2 or 3 position of the pyridine ring.

10. A method for treating a patient suffering from a neurodegenerative disease, the method comprising administering to the patient an effective amount of a compound having the formula:

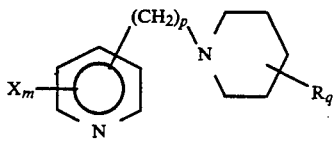

where R and X each represent a substituent other than hydrogen, m is an integer from 0–4, q is an integer from 0–10, p is an integer from 1–5, and the alkylpiperidine substituent is positioned at the 2 or 3 position of the pyridine ring.

11. The method of claim 9 or 10 whereby the effective amount of the compound is at least about 5 μg/kg patient weight, but does not exceed about 150 μg/kg patient weight.

12. The method of claim 9 or 10 whereby the effective amount of compound is administered to the patient in an amount of at least about 0.10 mg/hr/patient, but in an amount which does not exceed about 10 mg/hr/patient.

13. The method of claim 1, 5 or 9 whereby the compound is 2-pyridylethylpiperidine.

14. The method of claim 2, 6 or 10 whereby the compound is 3-pyridylmethylpyrrolidine.

15. The method of claim 1, 5 or 9 whereby R represents alkyl, and X represents alkyl or halo.

16. The method of claim 2, 6 or 10 whereby R represents alkyl, and X represents alkyl or halo.

17. The method of claim 15 whereby R is $C_1$ to $C_7$ alkyl.

18. The method of claim 16 whereby R is $C_1$ to $C_7$ alkyl.

* * * * *

UNITED STATES PATENT AND TRADEMARK OFFICE
CERTIFICATE OF CORRECTION

PATENT NO. : 5,214,060
DATED : May 25, 1993
INVENTOR(S) : William S. Caldwell and Patrick M. Lippiello It is certified that error appears in the above-indentified patent and that said Letters Patent is hereby corrected as shown below:

On the Cover Sheet under References Cited, please add
-- FOREIGN PATENT DOCUMENTS

0316718 EPC
    0377520 EPC --.

Signed and Sealed this

Seventh Day of February, 1995

Attest:

BRUCE LEHMAN

*Attesting Officer*      *Commissioner of Patents and Trademarks*